(12) United States Patent
Decoster et al.

(10) Patent No.: US 7,223,384 B1
(45) Date of Patent: *May 29, 2007

(54) COSMETIC COMPOSITIONS COMPRISING AT LEAST ONE SILICONE COPOLYMER AND AT LEAST ONE ADDITIONAL SILICONE, AND USES THEREOF

(75) Inventors: Sandrine Decoster, Saint Gratien (FR); Véronique Douin, Paris (FR); Virginie Bailly, Clichy (FR)

(73) Assignee: L'Oreal S.A., Paris (FR)

( * ) Notice: Subject to any disclaimer, the term of this patent is extended or adjusted under 35 U.S.C. 154(b) by 296 days.

This patent is subject to a terminal disclaimer.

(21) Appl. No.: 09/692,749

(22) Filed: Oct. 20, 2000

(30) Foreign Application Priority Data

Oct. 20, 1999 (FR) .................................. 99 13096

(51) Int. Cl.
 *A61K 8/00* (2006.01)
 *A61Q 5/12* (2006.01)
 *C11D 1/62* (2006.01)

(52) U.S. Cl. ............... 424/70.1; 424/70.27; 424/70.28; 514/63

(58) Field of Classification Search ............ 424/70.28, 424/70.1, 70.2, 70.6, 70.7, 70.12, 70.16, 424/70.19, 70.22, 70.01, 70.27; 510/120, 510/119; 514/63
See application file for complete search history.

(56) References Cited

U.S. PATENT DOCUMENTS

| | | | | |
|---|---|---|---|---|
| 2,528,378 A | | 10/1950 | Mannheimer ............. 260/309.6 |
| 2,781,354 A | | 2/1957 | Mannheimer ............. 260/309.6 |
| 4,693,935 A | | 9/1987 | Mazurek ..................... 428/352 |
| 4,728,571 A | | 3/1988 | Clemens et al. ............ 428/352 |
| 4,957,732 A | | 9/1990 | Grollier et al. ............... 424/73 |
| 4,972,037 A | | 11/1990 | Garbe et al. ................ 526/245 |
| 5,063,051 A | * | 11/1991 | Grollier et al. ............... 424/70 |
| 5,360,851 A | | 11/1994 | Feder et al. ................. 524/157 |
| 5,650,383 A | * | 7/1997 | Dubief et al. ............... 510/122 |
| 5,667,771 A | | 9/1997 | Carballada et al. ...... 424/70.12 |
| 5,929,173 A | * | 7/1999 | Midha et al. ............... 525/301 |
| 5,948,739 A | * | 9/1999 | Inman ........................ 510/122 |
| 6,011,126 A | * | 1/2000 | Dubief et al. ............... 525/477 |
| 6,039,936 A | * | 3/2000 | Restle et al. ............... 424/70.1 |

FOREIGN PATENT DOCUMENTS

| | | |
|---|---|---|
| EP | 0 186 507 | 7/1986 |
| EP | 0 342 834 | 11/1989 |
| EP | 0 412 704 | 2/1991 |
| EP | 0 412 707 | 2/1991 |
| EP | 0 582 152 | 2/1994 |
| EP | 0 874 017 | 10/1998 |
| FR | 2 589 476 | 5/1987 |
| WO | WO 93/23009 | 11/1993 |
| WO | WO 93/23446 | 11/1993 |
| WO | WO 95/00578 | 1/1995 |

OTHER PUBLICATIONS

M.R. Porter, "Handbook of Surfactants", Blackie & Son Ltd., Glasgow & London, 1991, pp. 116-178.
Dr. Otto Jacobi et al., "Investigation into the Reciprocal Action of Cosmetics and the Biosphere of the Stratum Corneum of the Skin", Cosmetics and Toiletries, vol. 91, Jan. 1976, pp. 25-32.
English language Derwent Abstract of FR 2 589 476.

* cited by examiner

*Primary Examiner*—Sreeni Padmanabhan
*Assistant Examiner*—Gina C. Yu
(74) *Attorney, Agent, or Firm*—Finnegan, Henderson, Farabow, Garrett & Dunner, L.L.P.

(57) ABSTRACT

Cosmetic compositions comprising, in a cosmetically acceptable medium, at least one silicone copolymer with a dynamic viscosity ranging from $1 \times 10^6$ to $100 \times 10^6$ cP and at least one additional silicone. This combination can give cosmetic properties, such as at least one of smoothness, lightness, and softness, without the phenomenon of regressing keratin fibers. These compositions can be used for washing and/or conditioning a keratin material, such as the hair or the skin.

112 Claims, No Drawings

COSMETIC COMPOSITIONS COMPRISING AT LEAST ONE SILICONE COPOLYMER AND AT LEAST ONE ADDITIONAL SILICONE, AND USES THEREOF

The present invention relates to novel cosmetic compositions comprising, in a cosmetically acceptable medium, at least one silicone copolymer defined below, with a dynamic viscosity ranging from $1 \times 10^6$ to $100 \times 10^6$ cP and at least one additional silicone.

It is well known that hair that has been sensitized (i.e. damaged and/or embrittled) to varying degrees under the action of atmospheric agents or mechanical or chemical treatments, such as dyes, bleaches and/or permanent-waving, can be often difficult to disentangle and to style, and may lack softness.

It has already been recommended to use conditioners, in particular cationic polymers or silicones, in compositions for washing or caring for keratin materials such as the hair, in order to facilitate the disentangling of the hair and to give it softness and suppleness. However, the cosmetic advantages mentioned above can be accompanied, on dried hair, by certain cosmetic effects considered undesirable, i.e., lankness of the hairstyle (lack of lightness of the hair) and lack of smoothness (hair not uniform from the root to the tip).

In addition, the use of cationic polymers for this purpose may have various drawbacks. On account of their high affinity for the hair, some of these polymers can become deposited thereon to a large extent during repeated use, and may lead to adverse effects such as an unpleasant, laden feel, stiffening of the hair and interfiber adhesion which may affect styling. These drawbacks may be more accentuated in the case of fine hair, which lacks liveliness and body.

In summary, it is found that the current cosmetic compositions comprising cationic silicones and/or cationic surfactants are not always entirely satisfactory.

The inventors have now discovered that the combination of at least one silicone copolymer defined below, with a dynamic viscosity ranging from $1 \times 10^6$ to $100 \times 10^6$ cP, with at least one additional silicone makes it possible to overcome at least one of these drawbacks.

Thus, after considerable research conducted in this matter, the inventors have found that by introducing at least one silicone copolymer with a dynamic viscosity ranging from $1 \times 10^6$ to $100 \times 10^6$ cP, into compositions, such as hair compositions containing at least one additional silicone, it is possible to limit, or even eliminate, the problems generally associated with the use of such compositions, i.e., for example, the lankness (charged feel following repeated applications) and the lack of smoothness and softness of the hair, while at the same time retaining at least one of the other advantageous cosmetic properties which are associated with conditioner-based compositions.

Moreover, when applied to the skin, for example in the form of a bubble bath or shower gel, the compositions of the invention can provide an improvement in the softness of the skin.

Thus, according to the present invention, cosmetic compositions are now proposed comprising, in a cosmetically acceptable medium, at least one silicone copolymer defined below, wherein said copolymer has a dynamic viscosity ranging from $1 \times 10^6$ to $100 \times 10^6$ cP, and at least one additional silicone.

Another subject of the invention relates to the use of at least one silicone copolymer defined below, with a dynamic viscosity ranging from $1 \times 10^6$ to $100 \times 10^6$ cP, in, or for the manufacture of, a cosmetic composition comprising at least one additional silicone.

The various subjects of the invention will now be described in detail. All the meanings and definitions of the compounds used in the present invention given below are valid for all the subjects of the invention.

The at least one silicone copolymer results from the addition reaction, in the presence of a catalyst, of at least:

(a) one polysiloxane of formula (I):

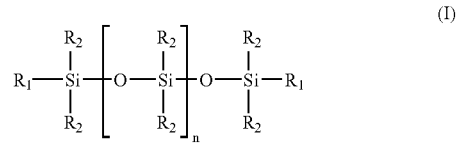

in which:

$R_1$, which may be identical or different, are independently chosen from groups that can react by chain addition reaction such as, for example, a hydrogen atom or aliphatic groups comprising an ethylenic unsaturation, such as vinyl, allyl and hexenyl groups;

$R_2$ in formula (I), which may be identical or different, are independently chosen from alkyl, alkenyl, cycloalkyl, aryl, hydroxyl, and alkylaryl groups, and can optionally further comprise functional groups chosen from ethers, amines, carboxyls, hydroxyls, thiols, esters, sulfonates and sulfates; wherein:

the alkyl groups comprise, for example, 1 to 20 carbon atoms; the alkenyl groups comprise, for example, from 2 to 10 carbon atoms; the cycloalkyl groups comprise, for example, 5 or 6 carbon atoms; the aryl groups comprise, for example, phenyl groups; and the alkylaryl groups comprise, for example, from 7 to 20 carbon atoms;

In one embodiment, $R_2$ is chosen from methyl.

n is an integer wherein the polysiloxane of formula (I) has a kinematic viscosity ranging from 1 to $1 \times 10^6$ mm$^2$/s, for example, n may range from 5 to 5000; and (b) at least one silicone compound comprising at least one and not more than two groups capable of reacting with the groups $R_1$ of the polysiloxane (a), wherein:

at least one of the compounds of type (a) and (b) comprises an aliphatic group, such as a $C_2$-$C_6$ aliphatic group, comprising an ethylenic unsaturation.

The compounds of type (b) can be another polysiloxane of type (a) in which at least one and not more than two groups $R_1$ of the polysiloxane (b) can react with the groups $R_1$ of the polysiloxane (a).

In one embodiment, the at least one silicone copolymer is obtained by addition reaction, in the presence of a hydrosilylation catalyst (for example a platinum catalyst), of at least:

(a) one α,ω-divinylpolydimethylsiloxane, and (b) one α,ω-dihydrogenopolydimethylsiloxane.

The silicone copolymer generally has a dynamic viscosity, measured at a temperature of about 25° C. and at a shear rate of 0.01 Hz for a stress of 1500 Pa, ranging from $1 \times 10^6$ to $100 \times 10^6$ cP, such as ranging from $5 \times 10^6$ cP to $30 \times 10^6$ cP.

All the dynamic viscosity measurements given in the present patent application were taken at a temperature of about 25° C., on a Carri-Medium CSL2-500 machine.

The kinematic viscosity is measured, for example, at 25° C. according to ASTM standard 445 Appendix C.

The at least one silicone copolymer according to the invention is essentially non-crosslinked, i.e., not crosslinked to an extent sufficient to be referred to as a crosslinked copolymer.

Another subject of the invention relates to compositions wherein the at least one silicone copolymer present in the composition is in the form of an aqueous emulsion.

The expression "aqueous emulsion" means an emulsion of oil-in-water type in which the at least one silicone copolymer is dispersed, such as in the form of particles or droplets, in the aqueous phase forming the continuous phase of the emulsion. This emulsion can be stabilized with a common emulsifying system.

This silicone emulsion can have a silicone droplet or particle size ranging from 10 nm to 50 µm, such as from 0.3 µm to 20 µm. The particle size is measured by laser granulometry.

The emulsifying system comprises at least one surfactant commonly used in silicone emulsions. These surfactants may be nonionic, cationic, anionic or amphoteric, or mixtures thereof, such as those described below.

The emulsifying system represents, for example, from 0.5% to 10% by weight relative to the total weight of the emulsion.

The synthesis of these silicone emulsions is described for example in patent application EP-A-874 017, the disclosure of which is incorporated by reference herein.

Such emulsions are sold for example under the name DC2-1997 Cationic Emulsion by the company Dow Corning. This emulsion comprises an α,ω-divinyl-dimethicone/α,ω-dihydrogenodimethicone copolymer with a dynamic viscosity of about 15×10⁶ cP, an emulsifier of cationic type such as cetyltrimethylammonium chloride, a stabilizer such as hydroxyethylcellulose, and water.

The at least one silicone copolymer can be present in a representative amount ranging from 0.05% to 10% by weight relative to the total weight of the composition, such as from 0.1% to 5% by weight relative to the total weight of the composition.

The aqueous emulsion of the at least one silicone copolymer can be present in a representative amount ranging from 0.5% to 15% by weight relative to the total weight of the composition.

The silicones, other than the silicone copolymer of the invention defined above that can be used in accordance with the invention can, for example, be chosen from polyorganosiloxanes that are insoluble in the composition and that can be chosen from oils, waxes, resins and gums.

Such polyorganosiloxanes, which can be volatile or non-volatile, are defined in greater detail in the book by Walter Noll "Chemistry and Technology of Silicones" (1968) Academic Press.

Volatile polyorganosiloxanes can be chosen from those having a boiling point ranging from 60° C. to 260° C., and, for example, chosen from:

(i) cyclic polyorganosiloxanes comprising from 3 to 7 and preferably from 4 to 5 silicon atoms. Such polyorganosiloxanes, for example, can be chosen from at least one octamethylcyclotetrasiloxane, sold for example under the name "Volatile Silicone 7207" by Union Carbide, and "Silbione 70045 V 2" by Rhone-Poulenc; and decamethylcyclopentasiloxane, sold under the name "Volatile Silicone 7158" by Union Carbide, and "Silbione 70045 V 5" by Rhone-Poulenc.

Mention may also be made of cyclocopolymers of the dimethylsiloxane/methylalkylsiloxane type, such as "Volatile Silicone FZ 3109" sold by the company Union Carbide, of chemical structure:

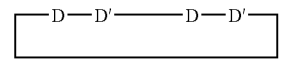

with D: 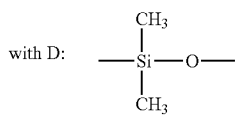 with D': 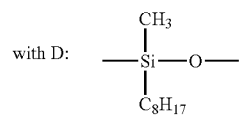

Mention may also be made of mixtures of cyclic polyorganosiloxanes with organosilicon compounds, such as the mixture of octamethylcyclotetrasiloxane and tetratrimethylsilylpentaerythritol, such as a 50/50 mixture, and the mixture of octamethylcyclotetrasiloxane and oxy-1,1'-bis(2,2,2',2',3,3'-hexatrimethylsilyloxy)neopentane;

(ii) linear volatile polyorganosiloxanes comprising from 2 to 9 silicon atoms with a kinematic viscosity of less than or equal to 5×10⁻⁶ m²/s at 25° C. This is, for example, decamethyltetrasiloxane, sold for example under the name "SH 200" by the company Toray Silicone. Silicones forming part of this category are also described in the article published in Cosmetics and Toiletries, Vol. 91, Jan. 76, pp. 27-32, Todd & Byers "Volatile Silicone Fluids for Cosmetics".

Non-volatile polyorganosiloxanes that can be used are chosen from polyalkylsiloxanes, polyarylsiloxanes, polyalkylarylsiloxanes, silicone gums, silicone resins, and polyorganosiloxanes modified with organofunctional groups, and mixtures thereof.

Non-volatile silicones are, for example, chosen from polyalkylsiloxanes, such as polydimethylsiloxanes that comprise trimethylsilyl end groups with a kinematic viscosity of from 5×10⁻⁶ to 2.5 m²/s at 25° C., such as from 1×10⁻⁵ to 1 m²/s. The kinematic viscosity of the silicones is measured, for example, at 25° C. according to ASTM standard 445 Appendix C.

Among these polyalkylsiloxanes, mention may be made, in a non-limiting manner, of the following commercial products:

the Silbione oils of the series 47 and 70 047 and the Mirasil oils sold by Rhône-Poulenc, such as, for example, the oil 70 047 V 500 000;

the oils of the Mirasil series sold by the company Rhône-Poulenc;

the oils of the 200 series from the company Dow Corning, such as, for example, DC200 with a viscosity of 60,000 Cst; and the Viscasil oils from General Electric and certain oils of the SF series (SF 96, SF 18) from General Electric.

Mention may also be made of polydimethyl-siloxanes comprising dimethylsilanol end groups (Dimethiconol according to the name given in the International Cosmetic Ingredient Dictionary and Handbook, hereafter "CTFA"), such as the oils of the 48 series from the company Rhône-Poulenc.

In this category of polyalkylsiloxanes, mention may also be made of the products sold under the names "Abil Wax 9800 and 9801" by the company Goldschmidt, which are poly($C_1$-$C_{20}$)alkylsiloxanes.

The polyalkylarylsiloxanes can be chosen, for example, from linear and branched polydimethyl-methylphenylsiloxanes and polydimethyldiphenylsiloxanes with a kinematic viscosity of from $1 \times 10^{-5}$ to $5 \times 10^{-2}$ m$^2$/s at 25° C.

Among these polyalkylarylsiloxanes, mention may be made, by way of example, of the products sold under the following names:
- the Silbione oils of the 70 641 series from Rhône-Poulenc;
- the oils of the Rhodorsil 70 633 and 763 series from Rhône-Poulenc;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Additionally, at least one silicone gum can be used in accordance with the invention. For example, polydiorganosiloxanes with high number-average molecular masses ranging from 200,000 and 1,000,000 can be used. When more than one silicone gum is used, at least one solvent chosen from volatile silicones, polydimethylsiloxane (PDMS) oils, polyphenylmethylsiloxane (PPMS) oils, isoparaffins, polyisobutylenes, methylene chloride, pentane, dodecane and tridecane is also used.

Mention may be made, for example, of the following products:
- polydimethylsiloxane,
- polydimethylsiloxane/methylvinylsiloxane gums,
- polydimethylsiloxane/diphenylsiloxane,
- polydimethylsiloxane/phenylmethylsiloxane, and
- polydimethylsiloxane/diphenylsiloxane/methylvinyl-siloxane.

Products which can be used, for example, in accordance with the invention are mixtures such as:
- mixtures formed from a polydimethylsiloxane hydroxylated at the end of the chain (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;
- mixtures formed from a polydimethylsiloxane gum and from a cyclic silicone, such as the product SF 1214 Silicone Fluid from the company General Electric; this product is an SF 30 gum corresponding to a dimethicone, having a number-average molecular weight of 500,000, dissolved in SF 1202 Silicone Fluid oil corresponding to decamethylcyclopentasiloxane;
- mixtures of two PDMSs of different viscosities, and for example of a PDMS gum and a PDMS oil, such as the product SF 1236 from the company General Electric. The product SF 1236 is a mixture of a gum SE 30 defined above, having a kinematic viscosity of 20 m$^2$/s, and an oil SF 96, with a kinematic viscosity of $5 \times 10^{-6}$ m$^2$/s. This product preferably contains 15% SE 30 gum and 85% SF 96 oil.

The organopolysiloxane resins which can be used in accordance with the invention are crosslinked siloxane systems comprising units chosen from: $R_2SiO_{2/2}$, $R_3SiO_{1/2}$, $RSiO_{3/2}$ and $SiO_{4/2}$ in which R is chosen from hydrocarbons comprising from 1 to 16 carbon atoms and phenyl groups. For example, the products in which R is chosen from $C_1$-$C_4$ alkyls can be used. And more specifically, R can be chosen from methyl, and phenyl groups.

Among these resins, mention may be made of the product sold under the name "Dow Corning 593" and those sold under the names "Silicone Fluid SS 4230 and SS 4267" by the company General Electric, and which are silicones of dimethyl/trimethyl siloxane structure.

Mention may also be made of the resins of the trimethylsiloxysilicate type sold for example under the names X22-4914, X21-5034 and X21-5037 by the company Shin-Etsu.

The organomodified silicones which can be used in accordance with the invention are silicones such as defined above comprising at least one organofunctional group attached by way of divalent hydrocarbon radicals.

Among the organomodified silicones, mention may be made of polyorganosiloxanes comprising:
- at least one group chosen from polyethylenoxy and polypropylenoxy groups optionally comprising $C_6$-$C_{24}$ alkyl groups, such as the products known as dimethicone copolyol sold by the company Dow Corning under the name DC 1248, and the oils Silwet L 722, L 7500, L 77 and L 711 from the company Union Carbide, and the ($C_{12}$)alkylmethicone copolyol sold by the company Dow Corning under the name Q2 5200;
- substituted and unsubstituted amine groups, such as the products sold under the name GP 4 Silicone Fluid and GP 7100 by the company Genesee, and the products sold under the names Q2 8220 and Dow Corning 929 and 939 by the company Dow Corning. The substituted amine groups are chosen from, for example, $C_1$-$C_4$ aminoalkyl groups;
- quaternary ammonium groups, such as the products sold under the names Abilquat 3272 and Abilquat 3474 by the company Goldschmidt;
- thiol groups, such as the products sold under the names "GP 72 A" and "GP 71" from Genesee;
- alkoxylated groups, such as the product sold under the name "Silicone Copolymer F-755" by SWS Silicones and Abil Wax 2428, 2434 and 2440 by the company Goldschmidt;
- hydroxyalkyl groups, such as the polyorganosiloxanes comprising at least one hydroxyalkyl function, described in French patent application FR-A-85/16334, the disclosure of which is incorporated by reference herein, corresponding to formula (IX):

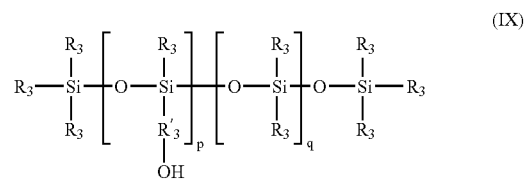

in which the radicals $R_3$, which may be identical or different, are independently chosen from methyl and phenyl radicals, wherein at least 60 mol % of the radicals $R_3$ are methyl; the radical $R'_3$ is chosen from divalent $C_2$-$C_{18}$ hydrocarbon-based alkylene chain units; p ranges from 1 to 30; q ranges from 1 to 150;

acyloxyalkyl groups such as, for example, the polyorganosiloxanes described in patent U.S. Pat. No. 4,957,732, the disclosure of which is incorporated by reference herein, and corresponding to formula (X):

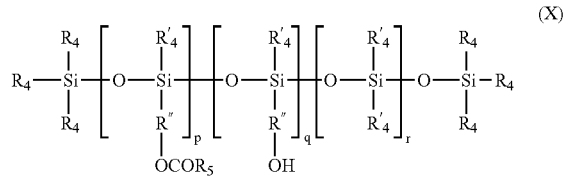

in which:

$R_4$, which may be identical or different, are independently chosen from methyl, phenyl, —OCOR$_5$ and hydroxyl groups, it being possible for only one of the radicals $R_4$ per silicon atom to be OH;

$R'_4$, which may be identical or different, are independently chosen from methyl and phenyl; and wherein at least 60 mol % of all of the radicals $R_4$ and $R'_4$ are chosen from methyl;

$R_5$ is chosen from $C_8$-$C_{20}$ alkyl and $C_8$-$C_{20}$ alkenyl groups; R", which may be identical or different, are independently chosen from linear and branched, divalent $C_2$-$C_{18}$ hydrocarbon-based alkylene radicals;

r ranges from 1 to 120;

p ranges from 1 to 30;

q ranges from 0 to less than 0.5 p, wherein the sum of p+q ranges from 1 to 30; provided that when the polyorganosiloxanes of formula (X) comprise groups:

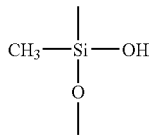

such groups are present in proportions not exceeding 15% of the sum p+q+r.

anionic groups of carboxylic type, such as, for example, in the products described in patent EP 186 507, the disclosure of which is incorporated by reference herein, from the company Chisso Corporation, or of alkylcarboxylic type, such as those present in the product X-22-3701 E from the company Shin-Etsu;

2-hydroxyalkyl sulfonate; 2-hydroxyalkyl thiosulfate such as the products sold by the company Goldschmidt under the names "Abil S201" and "Abil S255".

hydroxyacylamino groups, such as the polyorganosiloxanes described in patent application EP 342 834, the disclosure of which is incorporated by reference herein. Mention may be made, for example, of the product Q2-8413 from the company Dow Corning.

Additional silicones that can also be used according to the invention are silicones comprising a polysiloxane and a non-silicone organic chain, wherein either the polysiloxane or the non-silicone organic chain is considered the main chain of the polymer and the other is grafted onto said main chain. These polymers are described, for example, in patent applications EP-A-412,704, EP-A-412,707, EP-A-640,105, WO 95/00578, EP-A-582,152 and WO 93/23009 and U.S. Pat. Nos. 4,693,935, 4,728,571 and 4,972,037, the disclosures of which are incorporated by reference herein. These polymers are preferably anionic or nonionic.

Such polymers are, for example, copolymers obtained by radical polymerization starting with the monomer mixture comprising:

a) 50 to 90% by weight of tert-butyl acrylate;

b) 0 to 40% by weight of acrylic acid;

c) 5 to 40% by weight of silicone macromer of formula:

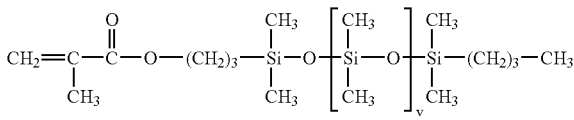

with v being a number ranging from 5 to 700; the weight percentages being calculated relative to the total weight of the monomers.

Other examples of grafted silicone polymers are, for example, polydimethylsiloxanes (PDMS) onto which are grafted, via a connecting chain unit of thiopropylene type, mixed polymer units of poly(meth)acrylic acid type and of polyalkyl (meth)acrylate type and polydimethylsiloxanes (PDMS) onto which are grafted, via a connecting chain unit of thiopropylene type, polymer units of polyisobutyl(meth)acrylate type.

According to the invention, all of the silicones can also be used in a form chosen from emulsions, nanoemulsions and microemulsions.

The polyorganosiloxanes that can be used in accordance with the invention are, for example:

nonvolatile silicones chosen from (1) polyalkylsiloxanes comprising trimethylsilyl end groups, such as oils with a kinematic viscosity ranging from 0.2 to 2.5 m²/s at 25° C., such as the oils of the series DC200 from Dow Corning, for example, one with a viscosity of 60,000 Cst, of the series Silbione 70047 and 47 and more particularly the oil 70 047 V 500 000, which are sold by the company Rhône-Poulenc; (2) polyalkylsiloxanes comprising dimethylsilanol end groups, such as dimethiconol; (3) polyalkylarylsiloxanes such as the oil Silbione 70641 V 200 sold by the company Rhône-Poulenc; (4) the organopolysiloxane resin sold under the name Dow Corning 593; (5) polysiloxanes comprising amine groups, such as amodimethicones and trimethylsilylamodimethicones; and (6) polysiloxanes comprising quaternary ammonium groups.

According to the invention, the at least one additional silicone can be present in an amount ranging from 0.001% to 20% by weight, such as from 0.01% to 10% by weight and further such as from 0.1% to 3% by weight, relative to the total weight of the final composition.

The compositions of the invention can also comprise at least one surfactant chosen from anionic, amphoteric and nonionic surfactants, which is generally present in an amount ranging from approximately 0.1% to 60% by weight relative to the total weight of the composition, such as from 3% to 40% and further such as from 5% to 30%.

The at least one surfactant chosen from anionic, amphoteric and nonionic surfactants, which are suitable for carrying out the present invention, are, for example, the following:

(i) Anionic Surfactant(s):

In the context of the present invention, their nature is not of critical importance.

Representative anionic surfactants include salts (for example alkaline salts, such as sodium salts, ammonium salts, amine salts, amino alcohol salts and magnesium salts) of the following compounds: alkyl sulfates, alkyl ether sulfates, alkylamidoether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates. The alkyl and acyl radicals of all of these various compounds can for example comprise from 8 to 24 carbon atoms, and the aryl radicals can for example be chosen from phenyl and benzyl groups.

For example, anionic surfactants can be chosen from fatty acid salts such as the salts of oleic, ricinoleic, palmitic and stearic acids, coconut oil acid and hydrogenated coconut oil acid and acyl lactylates in which the acyl radical comprises from 8 to 20 carbon atoms. At least one weakly anionic surfactant can also be used, such as alkyl-D-galactosiduronic acids and their salts, as well as polyoxyalkylenated $(C_6-C_{24})$ alkyl ether carboxylic acids, polyoxyalkylenated $(C_6-C_{24})$ alkylaryl ether carboxylic acids, polyoxyalkylenated $(C_6-C_{24})$ alkylamido ether carboxylic acids and their salts, for example, those comprising from 2 to 50 ethylene oxide groups.

As a further example, the anionic surfactant can be at least one salt chosen from alkyl sulfate salts and alkyl ether sulfate salts.

(ii) Nonionic Surfactant(s):

Useful nonionic surfactants include compounds that are well known per se (see for example in this respect "Handbook of Surfactants" by M. R. Porter, published by Blackie & Son (Glasgow and London), 1991, pp. 116-178), the disclosure of which is incorporated by reference herein, and, in the context of the present invention, their nature is not a critical feature. Thus, nonionic surfactants can include polyethoxylated, polypropoxylated and polyglycerolated fatty acids, alkylphenols, α-diols and alcohols having a fatty aliphatic chain comprising, for example, 8 to 18 carbon atoms, it being possible for the number of ethylene oxide and propylene oxide groups to range for example from 2 to 50 and for the number of glycerol groups to range for example from 2 to 30. Mention may also be made of copolymers of ethylene oxide and of propylene oxide, condensates of ethylene oxide and of propylene oxide with fatty alcohols; polyethoxylated fatty amides for example comprising from 2 to 30 mol of ethylene oxide, polyglycerolated fatty amides comprising on average 1 to 5, such as from 1.5 to 4, glycerol groups; polyethoxylated fatty amines for example comprising from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides such as $(C_{10}-C_{14})$alkylamine oxides and N-acylaminopropylmorpholine oxides. It will be noted that the alkylpolyglycosides are nonionic surfactants that can be suitable in the context of the present invention.

(iii) Amphoteric Surfactant(s):

Representative amphoteric surfactants, whose nature is not a critical feature in the context of the present invention, can be chosen from aliphatic secondary and tertiary amine derivatives in which the aliphatic radical is chosen from linear and branched chain radicals comprising 8 to 22 carbon atoms and comprising at least one water-soluble anionic group (chosen for example from carboxylate, sulfonate, sulfate, phosphate and phosphonate); mention may also be made of $(C_8-C_{20})$alkylbetaines, sulfobetaines, $(C_8-C_{20})$alkylamido$(C_1-C_6)$alkylbetaines and $(C_8-C_{20})$alkylamido$(C_1-C_6)$alkylsulfobetaines.

Representative amine derivatives include the products sold under the name Miranol, as described in U.S. Pat. Nos. 2,528,378 and 2,781,354, the disclosures of which are incorporated by reference herein, and having the structures:

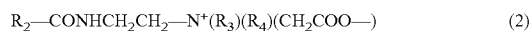

$$R_2-CONHCH_2CH_2-N^+(R_3)(R_4)(CH_2COO-) \quad (2)$$

in which:

$R_2$ is chosen from alkyl radicals derived from an acid $R_2$—COOH present in hydrolysed coconut oil, heptyl, nonyl and undecyl radicals, $R_3$ is chosen from β-hydroxyethyl groups, and $R_4$ is chosen from carboxymethyl groups;

and

$$R_5-CONHCH_2CH_2-N(B)(C) \quad (3)$$

in which:

(B) is —CH$_2$CH$_2$OX', with X' chosen from a —CH$_2$CH$_2$—COOH group and a hydrogen atom, (C) is —(CH$_2$)$_z$—Y', with z 1 or 2, and with Y' chosen from —COOH and —CH$_2$—CHOH—SO$_3$H radicals, $R_5$ is chosen from alkyl radicals, such as (a) alkyl radicals of an acid $R_5$—COOH present in oils chosen from coconut oil and hydrolysed linseed oil, (b) alkyl radicals, such as $C_7$, $C_9$, $C_{11}$ and $C_{13}$ alkyl radicals, and (c) $C_{17}$ alkyl radicals and the iso forms, and unsaturated $C_{17}$ radicals.

Such representative compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

By way of example, mention may be made of the cocoamphodiacetate sold under the trade name Miranol C2M Concentrate by the company Rhône-Poulenc.

In the compositions in accordance with the invention, at least two surfactants of different types can be used. Representative compositions include compositions comprising (a) more than one anionic surfactant, (b) at least one anionic surfactant and at least one amphoteric surfactant, and (c) at least one anionic surfactant and at least one nonionic surfactant. In one embodiment, the composition can comprise at least one anionic surfactant and at least one amphoteric surfactant.

The at least one anionic surfactant used for example, can be chosen from $(C_{12}-C_{14})$alkyl sulfates of sodium, of triethanolamine and of ammonium; $(C_{12}-C_{14})$alkyl ether sulfates of sodium, of triethanolamine and of ammonium, oxyethylenated with 2.2 mol of ethylene oxide; sodium cocoyl isethionate; and sodium $(C_{14}-C_{16})$-α-olefin sulfonate, and used in combination with an amphoteric surfactant chosen from either:

amphoteric surfactants such as the amine derivatives known as disodium cocoamphodipropionate and sodium cocoamphopropionate, sold for example by the company Rhone-Poulenc under the trade name "Miranol C2M Conc®" as an aqueous solution comprising 38% active material, and under the name Miranol C32; or amphoteric surfactants of zwitterionic type, such as alkylbetaines, for example the cocobetaine sold under the name "Dehyton AB 30" as an aqueous solution comprising 32% AM by the company Henkel.

In one embodiment of the invention, the compositions can also comprise at least one cationic surfactant.

Representative at least one cationic surfactants can be chosen from salts of optionally polyoxyalkylenated primary, secondary and tertiary fatty amines; quaternary ammonium salts; imidazoline derivatives; and amine oxides of cationic nature.

The cationic surfactants may, for example, be chosen from:

A) quaternary ammonium salts of formula (IV) below:

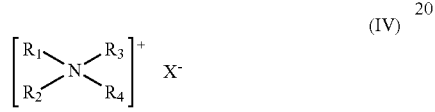

(IV)

in which:
the radicals $R_1$, $R_2$, $R_3$, and $R_4$, which may be identical or different, are independently chosen from linear and branched aliphatic radicals comprising from 1 to 30 carbon atoms, and aromatic radicals, such as $C_6$-$C_{20}$ aromatic radicals (for example, aryl and alkylaryl), wherein the aliphatic radicals can comprise hetero atoms such as, oxygen, nitrogen, sulfur and halogens, and wherein the aliphatic radicals are chosen, for example, from alkyl, alkoxy, polyoxy ($C_2$-$C_6$)alkylene, alkylamide, ($C_{12}$-$C_{22}$)alkylamido ($C_2$-$C_6$)alkyl, ($C_{12}$-$C_{22}$)alkylacetate and hydroxyalkyl radicals, comprising from 1 to 30 carbon atoms;

$X^-$ is an anion chosen from halides, phosphates, anions derived from organic acids, ($C_2$-$C_6$)alkyl sulfates, alkyl sulfonates, and alkylaryl sulfonates.

The compounds of formula (IV) can be chosen from, for example, (a) compounds comprising at least two fatty aliphatic radicals comprising from 8 to 30 carbon atoms, (b) compounds comprising at least one fatty aliphatic radical comprising from 17 to 30 carbon atoms, and (c) compounds comprising at least one aromatic radical.

B) Quaternary ammonium salts of imidazolinium, such as, for example, the salts of formula (V) below:

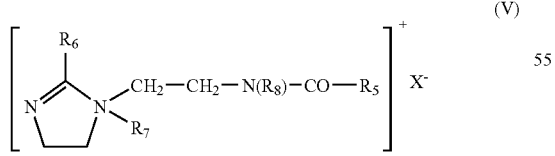

(V)

in which:
$R_5$ is chosen from alkenyl and alkyl radicals comprising from 8 to 30 carbon atoms, for example radicals derived from tallow fatty acid, $R_6$ is chosen from a hydrogen atom, $C_1$-$C_4$ alkyl radicals, and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, $X^-$ is an anion chosen from halides, phosphates, acetates, lactates, alkyl sulfates, alkyl sulfonates, and alkylaryl sulfonates.

For example, $R_5$ and $R_6$, which may be identical or different, are independently chosen from alkenyl and alkyl radicals comprising from 12 to 21 carbon atoms, for example, radicals derived from tallow fatty acid, $R_7$ is methyl, and $R_8$ is hydrogen.

Such products are, for example, (1) Quaternium-27 (International Cosmetic Ingredient Dictionary and Handbook, hereafter "CTFA", 1997), i.e., "Rewoquat" W75, W75PG, and W90, and (2) Quaternium-83 (CTFA 1997), i.e., "Rewoquat" W75HPG, which are sold by the company Witco.

C) Diquaternary ammonium salts of formula (VI):

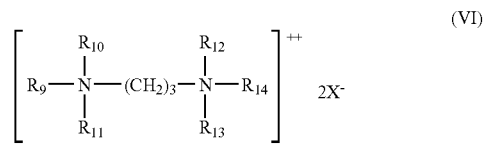

(VI)

in which:
$R_9$ is chosen from aliphatic radicals comprising from 16 to 30 carbon atoms, $R_{10}$, $R_{11}$, $R_{12}$, $R_{13}$ and $R_{14}$, which may be identical or different, are independently chosen from a hydrogen atom and alkyl radicals comprising from 1 to 4 carbon atoms, and $X^-$ is an anion chosen from halides, acetates, phosphates, nitrates and methyl sulfates.

For example, such diquaternary ammonium salts can comprise propane tallow diammonium dichloride.

D) Quaternary ammonium salts comprising at least one ester function. The quaternary ammonium salts comprising at least one ester function that can be used according to the invention are, for example, those of formula (VII) below:

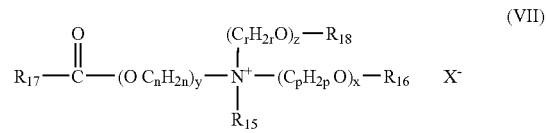

(VII)

in which:
$R_{15}$ is chosen from $C_1$-$C_6$ alkyl radicals and $C_1$-$C_6$ hydroxyalkyl and $C_1$-$C_6$ dihydroxyalkyl radicals;

$R_{16}$ is chosen from:
acyl groups of the following formula:

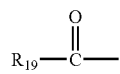

wherein $R_{19}$ is defined below,
linear and branched, saturated and unsaturated, $C_1$-$C_{22}$ hydrocarbon-based radicals, and
a hydrogen atom;
$R_{18}$ is chosen from:
acyl groups of the following formula:

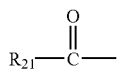

wherein $R_{21}$ is defined below,
linear and branched, saturated and unsaturated, $C_1$-$C_6$ hydrocarbon-based radicals, and
a hydrogen atom;
$R_{17}$, $R_{19}$ and $R_{21}$, which may be identical or different, are independently chosen from linear and branched, saturated and unsaturated, $C_7$-$C_{21}$ hydrocarbon-based radicals;
n, p and r, which may be identical or different, are independently integers ranging from 2 to 6;
y is an integer ranging from 1 to 10;
x and z, which may be identical or different, are independently integers ranging from 0 to 10;
$X^-$ is chosen from simple and complex, organic and inorganic anions;
provided that the sum x+y+z is from 1 to 15, and that when x is 0, then $R_{16}$ is chosen from linear and branched, saturated and unsaturated, $C_1$-$C_{22}$ hydrocarbon-based radicals, and that when z is 0, then $R_{18}$ is chosen from linear and branched, saturated and unsaturated, $C_1$-$C_6$ hydrocarbon-based radicals.

In one embodiment, the $R_{15}$ alkyl radicals may be linear and branched and further, for example, linear.

For example, $R_{15}$ may be chosen from methyl, ethyl, hydroxyethyl and dihydroxypropyl radicals and further for example from methyl and ethyl radicals.

The sum x+y+z may for example range from 1 to 10.

When $R_{16}$ is chosen from linear and branched, saturated and unsaturated, $C_1$-$C_{22}$ hydrocarbon-based radicals, $R_{16}$ may be long and comprise from 12 to 22 carbon atoms, or short and comprise from 1 to 3 carbon atoms.

When $R_{18}$ is chosen from linear and branched, saturated and unsaturated, $C_1$-$C_6$ hydrocarbon-based radicals, $R_{18}$ may for example comprise from 1 to 3 carbon atoms.

$R_{17}$, $R_{19}$ and $R_{21}$, which may be identical or different, can, for example, be independently chosen from linear and branched, saturated and unsaturated $C_{11}$-$C_{21}$ hydrocarbon-based radicals, and for example from linear and branched, saturated and unsaturated, $C_{11}$-$C_{21}$ alkyl and alkenyl radicals.

x and z, which may be identical or different, can for example independently be chosen from 0 or 1.

y for example may be equal to 1.

n, p and r, which may be identical or different, can for example be independently chosen from 2 and 3 and in one embodiment equal to 2.

The anion for example can be chosen from halides (chloride, bromide, and iodide) and alkyl sulfates, such as methyl sulfate. However, methanesulfonate, phosphate, nitrate, tosylate, anions derived from organic acids, such as acetate and lactate, and any other anions compatible with the ammonium comprising an ester function, may be used.

As a further example, the anion $X^-$ can be chosen from chloride and methyl sulfate.

Further examples of ammonium salts of formula (VII) are those in which:
$R_{15}$ is chosen from methyl and ethyl radicals,
x and y are equal to 1;
z is equal to 0 or 1;
n, p and rare equal to 2;
$R_{16}$ is chosen from:
acyl radicals

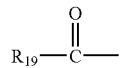

wherein $R_{19}$ is defined below,
methyl, ethyl and $C_{14}$-$C_{22}$ hydrocarbon-based radicals, and
a hydrogen atom;
$R_{18}$ is chosen from:
acyl radicals

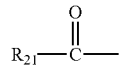

wherein $R_{21}$ is defined below,
a hydrogen atom;
$R_{17}$, $R_{19}$ and $R_{21}$, which may be identical or different, are independently chosen from linear and branched, saturated and unsaturated, $C_{13}$-$C_{17}$ hydrocarbon-based radicals, such as from linear and branched, saturated and unsaturated $C_{13}$-$C_{17}$ alkyl and alkenyl radicals.

The hydrocarbon-based radicals can for example be linear.

Representative compounds of formula (VII) are chosen from diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (for example chloride and methyl sulfate). The acyl radicals can for example comprise from 14 to 18 carbon atoms and can for example be obtained from plant oils, such as palm oil and sunflower oil. When the compound comprises several acyl radicals, these radicals, which may be independently chosen, may independently be identical or different.

These products are obtained, for example, by direct esterification of compounds chosen from triethanolamine, triisopropanolamine, alkyldiethanolamines and alkyldiisopropanolamines, which are optionally oxyalkylenated, with fatty acids or with fatty acid mixtures of plant or animal origin, and by transesterification of the methyl esters thereof. This esterification is followed by a quaternization using an alkylating agent such as alkyl halides (such ad methyl and ethyl halides), dialkyl sulfates (for example dimethyl and diethyl sulfates), methyl methanesulfonate, methyl para-toluenesulfonate, glycol chlorohydrin and glycerol chlorohydrin.

Such compounds are sold, for example, under the names Dehyquart by the company Henkel, Stepanquat by the company Stepan, Noxamium by the company Ceca and Rewoquat WE 18 by the company Rewo-Witco.

It is also possible to use the ammonium salts comprising at least one ester function, described in patents U.S. Pat. No.

4,874,554 and U.S. Pat. No. 4,137,180, the disclosures of which are incorporated by reference herein.

Representative quaternary ammonium salts of formula (IV) include tetraalkylammonium chlorides such as, for example, dialkyldimethylammonium chlorides and alkyltrimethylammonium chlorides, in which the alkyl radical comprises from 12 to 22 carbon atoms, for example behenyltrimethylammonium chloride, distearyidimethylammonium chloride, cetyltrimethylammonium chloride, and benzyldimethylstearylammonium chloride, and, stearamidopropyldimethyl(myristyl acetate)ammonium chloride sold under the name "Cepharyl 70" by the company Van Dyk.

According to the invention, the at least one cationic surfactant can for example be present in an amount ranging from 0.1% to 20% by weight relative to the total weight of the final composition, such as from 0.1% to 10%, from 0.5% to 7%, and further such as from 1% to 5% by weight relative to the total weight of the final composition.

The composition of the invention can also comprise at least one additive chosen from thickeners, fragrances, nacreous agents, preserving agents, silicone sunscreens, non-silicone sunscreens, vitamins, provitamins, cationic, amphoteric, anionic and nonionic polymers, proteins, protein hydrolysates, 18-methyleicosanoic acid, hydroxy acids, panthenol, ceramides, pseudoceramides, plant, animal, mineral and synthetic oils and any other additive conventionally used in cosmetics which does not substantially adversely affect the properties of the compositions according to the invention.

Generally, these additives are present in the composition according to the invention in amounts, for example, ranging from 0 to 20% by weight relative to the total weight of the composition. The precise amount of each additive is readily determined by those skilled in the art depending on its nature and its function.

The compositions in accordance with the invention can also be used for washing or treating at least one keratin material chosen from hair, skin, eyelashes, eyebrows, nails, lips, scalp, and hair.

The compositions according to the invention can also be a detergent composition chosen from shampoos, shower gels, bubble baths and make-up-removing products. In this embodiment of the invention, the compositions comprise a washing base, which is generally aqueous.

At least one surfactant forms the washing base and can be chosen from anionic, amphoteric, nonionic and cationic surfactants, such as those defined above.

The quantity and quality of the washing base are sufficient to give the final composition at least one of the following qualities, satisfactory foaming power and satisfactory detergent power.

According to the invention, the washing base can be present for example in an amount ranging from 4% to 50% by weight, such as from 6% to 35% by weight and even further such as from 8% to 25% by weight, relative to the total weight of the final composition.

Another subject of the invention is also a process for treating at least one keratin material, such as the skin and the hair, comprising applying a cosmetic composition as defined above to the at least one keratin material and optionally rinsing it out with water.

Thus, this process according to the invention allows maintenance of the hairstyle and treatment of, care of, washing of or removal of make-up from the skin, the hair or any other keratin material.

The compositions of the invention can for example be in forms chosen from rinse-out conditioners and leave-in conditioners; permanent-waving, straightening, dyeing and bleaching compositions; rinse-out compositions to be applied before a procedure chosen from dyeing, bleaching, permanent-waving and straightening the hair; rinse-out compositions to be applied after a procedure chosen from dyeing, bleaching, permanent-waving and straightening the hair; and rinse-out compositions to be applied between the two steps of a procedure chosen from permanent-waving and straightening the hair.

The compositions according to the invention can also be in a form chosen from aqueous and aqueous-alcoholic lotions for a care chosen from skin care and hair care.

The cosmetic compositions according to the invention can be in a form chosen from gels, milks, creams, emulsions, thickened lotions and mousses and can be used for treating at least one keratin material chosen from skin, nails, eyelashes, lips, and hair.

The compositions can be packaged in various forms chosen from vaporizers, pump-dispenser bottles and aerosol containers in order to ensure application of the composition in vaporized form or in the form of a mousse. Such packaging forms are indicated, for example, when it is desired to obtain a spray, a lacquer or a mousse for treating the hair.

In all of the text hereinabove and hereinbelow, the percentages expressed are on a weight basis.

The invention will now be illustrated more fully with the aid of the examples which follow, which should not be considered as limiting it to the embodiments described. In the examples, AM means active material.

EXAMPLE 1

A conditioner in accordance with the invention, having the following composition, was prepared:

| | |
|---|---|
| Mixture of myristyl, cetyl and stearyl myristate, palmitate and stearate | 1 g |
| Cetyl alcohol | 5 g |
| Hydroxyethylcellulose (MW 1,300,000) | 0.25 g |
| Behenyltrimethylammonium chloride (Genamin KDMP from Clariant) | 1 g AM |
| Cationic emulsion containing 67% AM of copolymer of polydimethylsiloxane containing α,ω-vinyl groups/polydimethylsiloxane containing α,ω-hydrogeno groups (DC-1997 from Dow Corning) | 0.8 g AM |
| Polydimethylsiloxane (Mirasil DM300 from Rhodia Chimie) | 5 g |
| Polydimethylsiloxane (DC200 Fluid-60,000 CS from Dow Corning) | 1 g |
| Fragrance, preserving agents | qs |
| Water | qs 100 g |

This composition is applied to washed and dried hair. It is left to stand on the hair for 2 minutes and is then rinsed off with water.

Hair treated with this conditioner is soft, smooth and disentangles easily.

EXAMPLE 2

A conditioner in accordance with the invention, having the following composition, was prepared:

| | |
|---|---|
| Cationic emulsion containing 67% AM of copolymer of polydimethylsiloxane containing α,ω-vinyl groups/polydimethylsiloxane containing α,ω-hydrogeno groups (DC-1997 from Dow Corning) | 0.7 g AM |
| SMDI/polyethylene glycol/alkyl (methyl/C18) endings copolymer at a concentration of 15% in a maltodextrin/water matrix (Aculyn 46 from Rohm & Haas) | 0.45 g AM |
| crosslinked ethyltrimethylammonium methacrylate chloride homopolymer as a reverse emulsion at a concentration of 50% in mineral oil (Salcare SC 95 from Ciba Geigy) | 0.55 g AM |
| Polydimethylsiloxane (Mirasil DM50 from Rhodia Chimie) | 1 g |
| Mixture of cetyl alcohol and of stearyl alcohol (50/50 by weight) | 6 g |
| Fragrance, preserving agents | qs |
| Water | qs 100 g |

What is claimed is:

1. A cosmetic composition comprising, in a cosmetically acceptable medium, (1) at least one silicone copolymer with a dynamic viscosity ranging from $1 \times 10^6$ to $100 \times 10^6$ cP, resulting from the addition reaction, in the presence of a catalyst, of:

(a) at least one polysiloxane of formula (I):

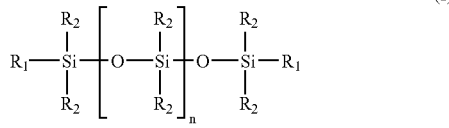

in which:

R$_1$, which may be identical or different, are independently chosen from groups that can react by chain addition reaction, R$_2$ in formula (I), which may be identical or different, are independently chosen from alkyl, alkenyl, cycloalkyl, aryl, hydroxyl, and alkylaryl groups, optionally comprising at least one functional group, n is an integer wherein the polysiloxane of formula (I) has a kinematic viscosity ranging from 1 to $1 \times 10^6$ mm$^2$/s; and (b) at least one silicone compound comprising at least one and not more than two groups capable of reacting with the groups R$_1$ of the polysiloxane (a), wherein:

at least one of the compounds of type (a) and (b) comprises an aliphatic group comprising an ethylenic unsaturation, (2) at least one additional silicone, and
(3) at least one cationic surfactant,
wherein the at least one additional silicone comprises an insoluble silicone.

2. A composition according to claim 1, wherein R$_1$ is chosen from a hydrogen atom and aliphatic groups comprising an ethylenic unsaturation.

3. A composition according to claim 2, wherein the aliphatic groups comprising an ethylenic unsaturation are chosen from vinyl, allyl and hexenyl groups.

4. A composition according to claim 1, wherein the groups R$_2$ are chosen from hydroxyl groups; alkyl groups comprising from 1 to 20 carbon atoms;

cycloalkyl groups comprising from 5 to 6 carbon atoms; phenyl groups; alkylaryl groups comprising from 7 to 20 carbon atoms; and can optionally further comprise functional groups chosen from ethers, amines, carboxyls, hydroxyls, thiols, esters, sulfonates and sulfates.

5. A composition according to claim 1, wherein said alkenyl groups are chosen from alkenyl groups comprising from 2 to 10 carbon atoms.

6. A composition according to claim 1, wherein R$_2$ is a methyl group.

7. A composition according to claim 1, wherein n is an integer ranging from 5 to 5,000.

8. A composition according to claim 1, wherein the compound of type (b) is another polysiloxane of type (a) in which at least one and not more than two groups R$_1$ of the polysiloxane (b) can react with the groups R$_1$ of the polysiloxane (a).

9. A composition according to claim 1, wherein, in the presence of a hydrosilylation catalyst, the at least one silicone copolymer is obtained by addition reaction of at least:

(a) one α,ω-divinylpolydimethylsiloxane, and
(b) one α,ω-dihydrogenopolydimethylsiloxane.

10. A composition according to claim 9, wherein the hydrosilylation catalyst is a platinum catalyst.

11. A composition according to claim 1, wherein said at least one silicone copolymer is in the form of an aqueous emulsion.

12. A composition according to claim 1, wherein the at least one silicone copolymer is essentially non-crosslinked.

13. A composition according to claim 1, wherein the at least one silicone copolymer is present in an amount ranging from 0.05% to 10% by weight relative to the total weight of the composition.

14. A composition according to claim 13, wherein the at least one silicone copolymer is present in an amount ranging from 0.1% to 5% by weight relative to the total weight of the composition.

15. A composition according to claim 1, wherein the at least one additional silicone comprises insoluble silicones chosen from volatile and non-volatile polyorganosiloxanes.

16. A composition according to claim 1, wherein said at least one additional silicone is in a form chosen from emulsions, nanoemulsions and microemulsions.

17. A composition according to claim 15, wherein said at least one additional silicone is chosen from oils, waxes, resins and gums.

18. A composition according to claim 15, wherein said volatile polyorganosiloxanes are chosen from cyclic polyorganosiloxanes comprising from 3 to 7 silicon atoms, and linear volatile silicones comprising 2 to 9 silicon atoms, with a kinematic viscosity of less than or equal to $5 \times 10^{-6}$ m$^2$/s at 25° C.

19. A composition according to claim 18, wherein said volatile polyorganosiloxanes are chosen from cyclic polyorganosiloxanes comprising from 4 to 5 silicon atoms.

20. A composition according to claim 18, wherein said cyclic polyorganosiloxanes are chosen from octamethylcyclotetrasiloxane, dimethylsiloxane/methylalkylsiloxane cyclocopolymers, and mixtures of cyclic silicones with organosilicon compounds.

21. A composition according to claim 20, wherein said dimethylsiloxane/methylalkylsiloxane cyclocopolymers are chosen from cyclocopolymers of the following structure:

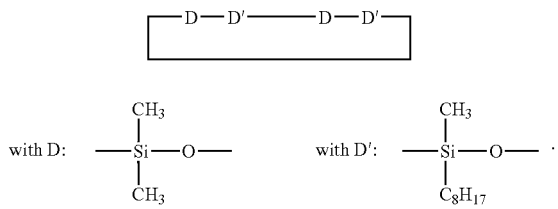

22. A composition according to claim 20, wherein said mixtures of cyclic silicones with organosilicon compounds are chosen from a mixture of octamethylcyclotetrasiloxane and tetratrimethylsilylpentaerythritol and a mixture of octamethylcyclotetrasiloxane and oxy-1,1'-bis(2,2,2',2',3,3'-hexatrimethylsilyloxy)neopentane.

23. A composition according to claim 18, wherein said linear volatile silicone is decamethyltetrasiloxane.

24. A composition according to claim 15, wherein said non-volatile polyorgano-siloxanes are chosen from poly-alkylsiloxanes, polyarylsiloxanes, polyalkylaryl-siloxanes, silicone gums, silicone resins, and polyorgano-siloxanes modified with organofunctional groups.

25. A composition according to claim 24, wherein:
(a) the polyalkylsiloxanes are chosen from:
polydimethylsiloxanes comprising trimethylsilyl end groups;
polydimethylsiloxanes comprising dimethylsilanol end groups; and
poly($C_1$-$C_{20}$)alkylsiloxanes;
(b) the polyalkylarylsiloxanes are chosen from:
linear and branched polydimethylmethylphenylsiloxanes;
(c) the silicone gums are chosen from polydiorgano-siloxanes with number-average molecular masses ranging from 200,000 to 1,000,000;
(d) the resins are chosen from resins comprising units chosen from $R_3SiO_{1/2}$, $R_2SiO_{2/2}$, $RSiO_{3/2}$, and $SiO_{4/2}$, wherein R is chosen from hydrocarbon-based groups comprising from 1 to 16 carbon atoms and phenyl groups; and
(e) the polyorgano-siloxanes modified with organofunctional groups are chosen from silicones comprising at least one organofunctional group attached by way of a hydrocarbon-based radical.

26. A composition according to claim 25, wherein the polydimethylmethylphenylsiloxanes are chosen from polydimethyldiphenylsiloxanes with a kinematic viscosity ranging from $1 \times 10^{-5}$ to $5 \times 10^{-2}$ m$^2$/s at 25° C.

27. A composition according to claim 25, wherein the silicone gums are chosen from:
poly[(dimethylsiloxane)/(methylvinylsiloxane)],
poly[(dimethylsiloxane)/(diphenylsiloxane)],
poly[(dimethylsiloxane)/(phenylmethylsiloxane)], and
poly[(dimethylsiloxane)/(diphenylsiloxane)/(methylvinylsiloxane)] and the following mixtures:
mixtures formed from a polydimethylsiloxane which is hydroxylated at the end of the chain and from a cyclic polydimethylsiloxane;
mixtures formed from a polydimethylsiloxane gum and from a cyclic silicone; and
mixtures of polydimethylsiloxanes of different viscosities.

28. A composition according to claim 25, wherein said R of said resins is chosen from $C_1$-$C_4$ alkyls and phenyl.

29. A composition according to claim 28, wherein said R of said at least one resin is chosen from methyl.

30. A composition according to claim 24, wherein said polyorgano-siloxanes modified with organofunctional groups are chosen from polyorgano-siloxanes comprising:
a) at least one group chosen from polyethylenoxy and polypropylenoxy groups optionally comprising $C_6$-$C_{24}$ alkyl groups:
b) substituted and unsubstituted amine groups,
c) thiol groups,
d) alkoxylated groups,
e) hydroxyalkyl groups,
f) acyloxyalkyl groups,
g) alkylcarboxylic groups,
h) 2-hydroxyalkyl sulphonate groups,
i) 2-hydroxyalkyl thiosulfate groups,
j) hydroxyacylamino groups, and
k) quaternary ammonium groups.

31. A composition according to claim 30, wherein said substituted amine groups are chosen from $C_1$-$C_4$ alkylamino groups.

32. A composition according to claim 30, wherein said polyorgano-siloxanes comprising hydroxyalkyl groups are chosen from polyorganosiloxanes comprising at least one hydroxyalkyl function corresponding to formula (IX):

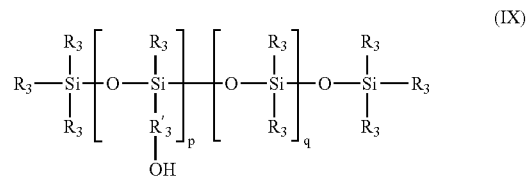

in which the radicals $R_3$, which may be identical or different, are independently chosen from methyl and phenyl radicals, wherein at least 60 mol % of the radicals $R_3$ are methyl;
the radical $R'_3$ is chosen from divalent $C_2$-$C_{18}$ hydrocarbon-based alkylene chain units; p ranges from 1 to 30; and q ranges from 1 to 150.

33. A composition according to claim 30, wherein said polyorgano-siloxanes modified with acyloxyalkyl groups are chosen from polyorganosiloxanes of formula (X):

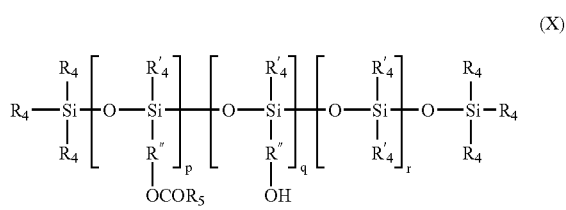

in which:
$R_4$, which may be identical or different, are independently chosen from methyl, phenyl, —OCOR$_5$ and hydroxyl groups, wherein it is optional for only one of the radicals $R_4$ per silicon atom to be OH;
$R_{14}$, which may be identical or different, are independently chosen from methyl and phenyl; and wherein at least 60 mol % of all of the radicals $R_4$ and $R'_4$ are chosen from methyl;

$R_5$ is chosen from $C_8$-$C_{20}$ alkyl and $C_8$-$C_{20}$ alkenyl groups;
R" is chosen from linear and branched, divalent $C_2$-$C_{18}$ hydrocarbon-based alkylene radicals;
r ranges from 1 to 120;
p ranges from 1 to 30;
q ranges from 0 to less than 0.5 p, wherein the sum of p+q ranges from 1 to 30;
provided that when the polyorganosiloxanes of formula (X) comprise groups:

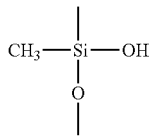

such groups are in proportions not exceeding 15% of the sum p+q+r.

34. A composition according to claim 15, wherein said at least one additional silicone is chosen from grafted silicone polymers.

35. A composition according to claim 34, wherein said grafted silicone polymers are chosen from silicones comprising a polysiloxane and a non-silicone organic chain, wherein either the polysiloxane or the non-silicone organic chain is considered the main chain of the polymer and the other is grafted onto said main chain.

36. A composition according to claim 35, wherein said grafted silicone polymers are chosen from copolymers obtained by radical polymerization starting with a monomer mixture comprising:
a) 50 to 90% by weight of tert-butyl acrylate;
b) 0 to 40% by weight of acrylic acid;
c) 5 to 40% by weight of silicone macromer of formula:

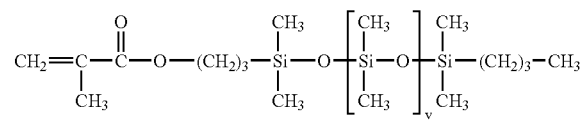

with v being a number ranging from 5 to 700; the weight percentages being calculated relative to the total weight of the monomers.

37. A composition according to claim 34, wherein said grafted silicone polymers are chosen from polydimethylsiloxanes (PDMS) onto which are grafted, via a connecting chain unit of thiopropylene type, mixed polymer units of poly(meth)acrylic acid type and of polyalkyl(meth)acrylate type and polydimethylsiloxanes (PDMS) onto which are grafted, via a connecting chain unit of thiopropylene type, polymer units of polyisobutyl(meth)acrylate type.

38. A composition according to claim 15, wherein the polyorgano-siloxanes are chosen from polyalkylsiloxanes comprising trimethylsilyl end groups, polyalkylsiloxanes comprising dimethylsilanol end groups, polyalkylaryl-siloxanes, mixtures of two PDMSs comprising a gum and an oil of different viscosities, mixtures of organosiloxanes and of cyclic silicones, polyorgano-siloxane resins, polysiloxanes comprising amine groups and polysiloxanes comprising quaternary ammonium groups.

39. A composition according to claim 1, wherein the at least one additional silicone is present in an amount ranging from 0.001% to 20% by weight relative to the total weight of the composition.

40. A composition according to claim 39, wherein the at least one additional silicone is present in an amount ranging from 0.01% to 10% by weight relative to the total weight of the composition.

41. A composition according to claim 1 wherein the at least one cationic surfactant is chosen from:
A) quaternary ammonium salts of formula (IV) below:

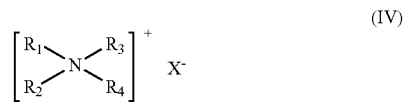

in which:
the radicals $R_1$, $R_2$, $R_3$, and $R_4$, which may be identical or different, are independently chosen from linear and branched aliphatic radicals comprising from 1 to 30 carbon atoms, and aromatic radicals, wherein the aliphatic radicals optionally comprise hetero atoms, and
$X^-$ is an anion chosen from the group of halides, phosphates, anions derived from organic acids, ($C_2$-$C_6$)alkyl sulfates, alkyl sulfonates, and alkylaryl sulfonates;

B) quaternary ammonium salts of imidazolinium of formula (V) below:

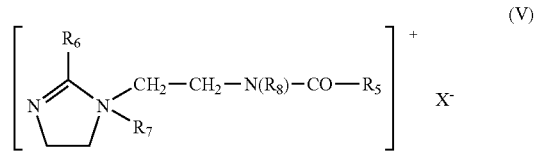

in which:
$R_5$ is chosen from alkenyl and alkyl radicals comprising from 8 to 30 carbon atoms,
$R_6$ is chosen from a hydrogen atom, $C_1$-$C_4$ alkyl radicals, and alkenyl and alkyl radicals comprising from 8 to 30 carbon atoms,
$R_7$ is chosen from $C_1$-$C_4$ alkyl radicals,
$R_8$ is chosen from a hydrogen atom and $C_1$-$C_4$ alkyl radicals, and
$X^-$ is an anion chosen from halides, phosphates, acetates, lactates, alkyl sulfates, alkyl sulfonates, and alkylaryl sulfonates;

C) diquaternary ammonium salts of formula (VI):

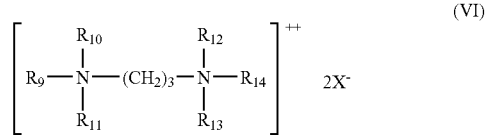

in which:
$R_9$ is chosen from aliphatic radicals comprising from 16 to 30 carbon atoms, $R_{10}$, $R_{11}$, $R_{12}$, $R_{13}$ and $R_{14}$, which may be identical or different, are independently chosen from a hydrogen atom and alkyl radicals comprising from 1 to 4 carbon atoms, and $X^-$ is an anion chosen from halides, acetates, phosphates, nitrates and methyl sulfates;

D) quaternary ammonium salts of formula (VII) below comprising at least one ester function:

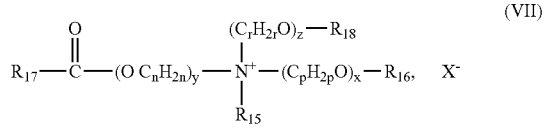

in which:

$R_{15}$ is chosen from $C_1$-$C_6$ alkyl radicals and $C_1$-$C_6$ hydroxyalkyl and $C_1$-$C_6$ dihydroxyalkyl radicals;

$R_{16}$ is chosen from:
  acyl groups of the following formula:

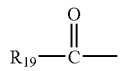

wherein $R_{19}$ is defined below,
  linear and branched, saturated and unsaturated, $C_1$-$C_{22}$ hydrocarbon-based radicals, and
  a hydrogen atom;

$R_{18}$ is chosen from:
  acyl groups of the following formula:

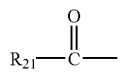

wherein $R_{21}$ is defined below,
  linear and branched, saturated and unsaturated, $C_1$-$C_6$ hydrocarbon-based radicals, and
  a hydrogen atom;

$R_{17}$, $R_{19}$ and $R_{21}$, which may be identical or different, are independently chosen from linear and branched, saturated and unsaturated, $C_7$-$C_{21}$ hydrocarbon-based radicals;

n, p and r, which may be identical or different, are independently integers ranging from 2 to 6;

y is an integer ranging from 1 to 10;

x and z, which may be identical or different, are independently integers ranging from 0 to 10; and $X^-$ is chosen from simple and complex, organic and inorganic anions; and provided that the sum x+y+z is from 1 to 15, and that when x is 0, then $R_{16}$ is chosen from linear and branched, saturated and unsaturated, $C_1$-$C_{22}$ hydrocarbon-based radicals, and that when z is 0, then $R_{18}$ is chosen from linear and branched, saturated and unsaturated, $C_1$-$C_6$ hydrocarbon-based radicals.

42. A composition according to claim 41, wherein said at least one cationic surfactant is chosen from:

A) quaternary ammonium salts of formula (IV) below:

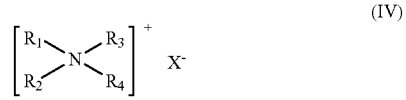

wherein:

$X^-$ is an anion chosen from halides, ($C_2$-$C_6$)alkyl sulfates, phosphates, alkyl and alkylaryl sulfonates, and anions derived from organic acids, and i)—the radicals $R_1$, $R_2$, and $R_3$, which may be identical or different, are independently chosen from linear and branched aliphatic radicals comprising from 1 to 4 carbon atoms, optionally comprising hetero atoms, and aromatic radicals, and $R_4$ is chosen from linear and branched alkyl radicals comprising from 16 to 30 carbon atoms;

ii)—the radicals $R_1$ and $R_2$, which may be identical or different, are independently chosen from linear and branched aliphatic radicals comprising from 1 to 4 carbon atoms, optionally comprising hetero atoms, and aromatic radicals, and $R_3$ and $R_4$, which may be identical or different, are independently chosen from linear and branched alkyl radicals comprising from 12 to 30 carbon atoms, wherein said radicals further comprise at least one function chosen from ester and amide functions.

43. A composition according to claim 41, wherein in said quaternary ammonium salts of formula (VII):

$R_{15}$ is chosen from methyl and ethyl radicals, x and y are equal to 1;

z is equal to 0 or 1;

n, p and r are equal to 2;

$R_{16}$ is chosen from:
  acyl radicals

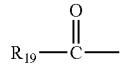

wherein $R_{19}$ is defined below,
  methyl, ethyl and $C_{14}$-$C_{22}$ hydrocarbon-based radicals, and
  a hydrogen atom;

$R_{18}$ is chosen from:
  acyl radicals

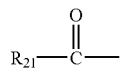

wherein $R_{21}$ is defined below,
  a hydrogen atom; and $R_{17}$, $R_{19}$ and $R_{21}$, which may be identical or different, are independently chosen from linear and branched, saturated and unsaturated, $C_{13}$-$C_{17}$ hydrocarbon-based radicals.

44. A composition according to claim 43, wherein $R_{17}$, $R_{19}$ and $R_{21}$ are chosen from linear and branched, saturated and unsaturated $C_{13}$-$C_{17}$ aliphatic radicals.

45. A composition according to claim 43, wherein the hydrocarbon-based radicals are chosen from linear hydrocarbon-based radicals.

46. A composition according to claim 41, wherein the compounds of formula (VII) are chosen from diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts.

47. A composition according to claim 46, wherein said monoacyloxyethyl-hydroxyethyldimethylammonium salts are chosen from monoacyloxyethyl-hydroxyethyldimethylammonium chloride salts and monoacyloxyethyl-hydroxyethyldimethylammonium methyl sulfate salts.

48. A composition according to claim 43, wherein when $R_{16}$ and $R_{18}$ are chosen from acyl radicals, said acyl radicals are obtained from plant oils chosen from palm oil and sunflower oil.

49. A composition according to claim 41, wherein $X^-$ of said quaternary ammonium salts of formula (IV) is an anion chosen from chloride, bromide, iodide, methyl sulfate, acetate, and lactate.

50. A composition according to claim 41, wherein said aromatic radicals of said quaternary ammonium salts of formula (IV) are chosen from aryl and alkylaryl.

51. A composition according to claim 41, wherein said hetero atoms of said quaternary ammonium salts of formula (IV) are chosen from oxygen, nitrogen, sulfur and halogens.

52. A composition according to claim 42, wherein said aliphatic radicals of formula (IV)(ii) are chosen from alkyl, alkoxy, alkylamide, polyoxy($C_2$-$C_6$)alkylene, and hydroxyalkyl radicals comprising from 1 to 4 carbon atoms.

53. A composition according to claim 42, wherein said $R_3$ and $R_4$ of formula (IV)(ii) are chosen from ($C_{12}$-$C_{22}$)alkylamido($C_2$-$C_6$)alkyl and ($C_{12}$-$C_{22}$)alkylacetate radicals.

54. A composition according to claim 41, wherein said $R_5$ of formula (V) is chosen from radicals derived from tallow fatty acid.

55. A composition according to claim 41, wherein in said quaternary ammonium salts of imidazolinium of formula (V):
  $R_5$ and $R_6$, which may be identical or different, are independently chosen from alkenyl and alkyl radicals comprising from 12 to 21 carbon atoms,
  $R_7$ is methyl, and
  $R_8$ is hydrogen.

56. A composition according to claim 55, wherein said $R_5$ and $R_6$, which may be identical or different, are independently chosen from radicals derived from tallow fatty acid.

57. A composition according to claim 41, wherein said diquaternary ammonium salts comprise propane tallow diammonium dichloride.

58. A composition according to claim 41, wherein said $R_{15}$ alkyl radicals of said quaternary ammonium salts of formula (VII) are chosen from linear and branched $C_1$-$C_6$ alkyl radicals.

59. A composition according to claim 58, wherein said $R_{15}$ radicals are linear radicals.

60. A composition according to claim 59, wherein said $R_{15}$ radicals are chosen from methyl, ethyl, hydroxyethyl and dihydroxypropyl.

61. A composition according to claim 60, wherein said $R_{15}$ radicals are chosen from methyl and ethyl.

62. A composition according to claim 41, wherein said sum of x+y+z of said quaternary ammonium salts of formula (VII) ranges from 1-10.

63. A composition according to claim 41, wherein said quaternary ammonium salts of formula (IV) are chosen from (a) compounds comprising at least two fatty aliphatic radicals comprising from 8 to 30 carbon atoms,
  (b) compounds comprising at least one fatty aliphatic radical comprising from 17 to 30 carbon atoms, and
  (c) compounds comprising at least one aromatic radical.

64. A composition according to claim 41, wherein said at least one cationic surfactant is chosen from behenyltrimethylammonium salts, stearamidopropyldimethyl(myristyl acetate)ammonium salts, Quaternium-27 and Quaternium-83.

65. A composition according to claim 41, wherein the at least one cationic surfactant is present in an amount ranging from 0.1% to 10% by weight relative to the total weight of the composition.

66. A composition according to claim 65, wherein the at least one cationic surfactant is present in an amount ranging from 0.5% to 7% by weight relative to the total weight of the composition.

67. A composition according to claim 66, wherein the at least one cationic surfactant is present in an amount ranging from 1% to 5% by weight relative to the total weight of the composition.

68. A composition according to claim 1 further comprising at least one surfactant chosen from anionic, nonionic, and amphoteric surfactants.

69. A composition according to claim 68, wherein the at least one surfactant chosen from anionic, nonionic, and amphoteric surfactants is present in an amount ranging from 0.1% to 60% by weight, relative to the total weight of the composition.

70. A composition according to claim 69, wherein the at least one surfactant chosen from anionic, nonionic, and amphoteric surfactants is present in an amount ranging from 3% to 40% by weight, relative to the total weight of the composition.

71. A composition according to claim 70, wherein the at least one surfactant chosen from anionic, nonionic, and amphoteric surfactants is present in an amount ranging from 5% to 30% by weight, relative to the total weight of the composition.

72. A composition according to claim 68, wherein the at least one surfactant chosen from anionic, nonionic, and amphoteric surfactants comprises at least one anionic surfactant salt chosen from alkyl sulfates, alkyl ether sulfates, alkylamidoether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates.

73. A composition according to claim 68, wherein said at least one surfactant is chosen from anionic surfactants chosen from alkaline salts, sodium salts, ammonium salts, amine salts, amino alcohol salts and magnesium salts.

74. A composition according to claim 72, wherein said alkyl and acyl portions of radicals of said salts comprise 1 and from 8 to 24 carbon atoms, and said aryl portions of radicals of said salts are phenyl.

75. A composition according to claim 68, wherein said at least one surfactant is chosen from anionic surfactants chosen from fatty acid salts, acyl lactates wherein the acyl radical comprises 8 to 20 carbon atoms, and weakly anionic surfactants.

76. A composition according to claim 75, wherein said fatty acid salts are chosen from the salts of oleic acid, ricinoleic acid, palmitic acid, stearic acid, coconut oil acid and hydrogenated coconut oil acid.

77. A composition according to claim 68, wherein said at least one surfactant is chosen from anionic surfactants chosen from alkyl-D-galactosiduronic acids and their salts, polyoxyalkylenated ($C_6$-$C_{24}$) alkyl ether carboxylic acids and their salts, polyoxyalkylenated ($C_6$-$C_{24}$) alkylaryl ether carboxylic acids and their salts, and polyoxyalkylenated ($C_6$-$C_{24}$) alkylamido ether carboxylic acids and their salts.

78. A composition according to claim 75, wherein said weakly anionic surfactants comprise from 2 to 50 ethylene oxide groups.

79. A composition according to claim 72, wherein said at least one anionic surfactant salt is chosen from alkyl sulfates and alkyl ether sulfates.

80. A composition according to claim 68, wherein said at least one surfactant is chosen from nonionic surfactants chosen from polyethoxylated, polypropoxylated and polyglycerolated fatty acids, alkylphenols, α-diols and alcohols having a fatty aliphatic chain comprising 8 to 18 carbon atoms, wherein the number of ethylene oxide and propylene oxide groups ranges from 2 to 50 and the number of glycerol groups ranges from 2 to 30, copolymers of ethylene oxide and of propylene oxide, condensates of ethylene oxide and of propylene oxide with fatty alcohols, polyethoxylated fatty amides comprising from 2 to 30 mol of ethylene oxide, polyglycerolated fatty amides comprising on average 1 to 5 glycerol groups, polyethoxylated fatty amines comprising from 2 to 30 mol of ethylene oxide, oxyethylenated fatty acid esters of sorbitan comprising from 2 to 30 mol of ethylene oxide, fatty acid esters of sucrose, fatty acid esters of polyethylene glycol, alkylpolyglycosides, N-alkylglucamine derivatives, and amine oxides.

81. A composition according to claim 80, wherein said polyglycerolated fatty amides comprise on average 1.5 to 4 glycerol groups.

82. A composition according to claim 80, wherein said amine oxides are chosen from ($C_{10}$-$C_{14}$)alkylamine oxides and N-acylaminopropylmorpholine oxides.

83. A composition according to claim 80, wherein said nonionic surfactants are chosen from alkylpolyglycosides.

84. A composition according to claim 68, wherein said at least one surfactant is chosen from amphoteric surfactants chosen from aliphatic secondary and tertiary amine derivatives wherein the aliphatic radical is chosen from linear and branched chain radicals comprising 8 to 22 carbon atoms and comprising at least one water-soluble anionic group, ($C_8$-$C_{20}$)alkylbetaines, sulfobetaines, ($C_8$-$C_{20}$)alkylamido($C_1$-$C_6$)alkylbetaines; and ($C_8$-$C_{20}$)alkylamido($C_1$-$C_6$)alkylsulfobetaines.

85. A composition according to claim 84, wherein said at least one water-soluble anionic group is chosen from carboxylates, sulfonates, sulfates, phosphates and phosphonates.

86. A composition according to claim 84, wherein said amine derivatives are chosen from the compounds:

in which $R_2$ is chosen from alkyl radicals derived from an acid $R_2$—COOH present in hydrolysed coconut oil, heptyl, nonyl and undecyl radicals, $R_3$ is chosen from β3-hydroxyethyl groups, and $R_4$ is chosen from carboxymethyl groups;

and

in which (B) is —$CH_2CH_2OX'$ chosen form a —$CH_2CH_2$—COOH group and a hydrogen atom, (C) is —$(CH_2)_z$—Y', with z=1 or 2, and with Y' chosen from —COOH and —$CH_2$—CHOH—$SO_3H$ radicals, $R_5$ is chosen from alkyl radicals and unsaturated $C_{17}$ radicals.

87. A composition according to claim 86, wherein said alkyl radicals $R_5$ are chosen from (a) alkyl radicals of an acid $R_5$—COOH present in oils chosen from coconut oil and hydrolysed linseed oil, and (b) $C_{17}$ alkyl radicals and the iso forms.

88. A composition according to claim 86, wherein said alkyl radicals of said $R_5$ are chosen from alkyl radicals chosen from $C_7$, $C_9$, $C_{11}$ and $C_{13}$ alkyl radicals.

89. A composition according to claim 68, wherein said at least one surfactant is chosen from at least two surfactants of different types.

90. A composition according to claim 89, wherein said at least two surfactants of different types are chosen from (a) more than one anionic surfactant, (b) at least one anionic surfactant and at least one amphoteric surfactant, and (c) at least one anionic surfactant and at least one nonionic surfactant.

91. A composition according to claim 68, wherein said at least one surfactant is chosen from anionic surfactants chosen from ($C_{12}$-$C_{14}$)alkyl sulfates of sodium, of triethanolamine and of ammonium, ($C_{12}$-$C_{14}$)alkyl ether sulfates of sodium, of triethanolamine and of ammonium, oxyethylenated with 2.2 mol of ethylene oxide, sodium cocoyl isethionate, and sodium ($C_{14}$-$C_{16}$)-α-olefin sulfonate, and from an amphoteric surfactant chosen from either:

amine derivatives comprising disodium cocoamphodipropionate and sodium cocoamphopropionate, or amphoteric surfactants of zwitterionic type.

92. A composition according to claim 91, wherein said amphoteric surfactants of zwitterionic type are chosen from alkylbetaines.

93. A composition according to claim 92, wherein said alkylbetaines are chosen from cocobetaine.

94. A composition according to claim 1 further comprising at least one additive chosen from thickeners, fragrances, nacreous agents, preserving agents, silicone sunscreens, non-silicone sunscreens, vitamins, provitamins, cationic, amphoteric, anionic and nonionic polymers, proteins, protein hydrolysates, 18-methyleicosanoic acid, hydroxy acids, panthenol, ceramides, pseudoceramides, and plant, animal, mineral and synthetic oils.

95. A composition according to claim 94, wherein said at least one additive is present in an amount ranging from 0 to 20% by weight relative to the total weight of the composition.

96. A rinse-out conditioner, a leave-in conditioner, a composition for permanent-waving the hair, a composition for straightening the hair, a composition for dyeing the hair, a composition for bleaching the hair, a rinse-out composition to be applied before a procedure chosen from dyeing, bleaching, permanent-waving and straightening the hair, a rinse-out composition to be applied after a procedure chosen from dyeing, bleaching, permanent-waving and straightening the hair, a rinse-out composition to be applied between the two steps of a permanent-waving operation, a rinse-out composition to be applied between the two steps of a hair-straightening operation, a washing composition for the body, an aqueous lotion, an aqueous-alcoholic lotion, a gel, a milk, a cream, an emulsion, a thickened lotion, a mousse, or a detergent composition comprising a washing base comprising, in a cosmetically acceptable medium, (1) at least one silicone copolymer with a dynamic viscosity ranging from $1\times10^6$ to $100\times10^6$ cP, resulting from the addition reaction, in the presence of a catalyst, of:

(a) at least one polysiloxane of formula (I):

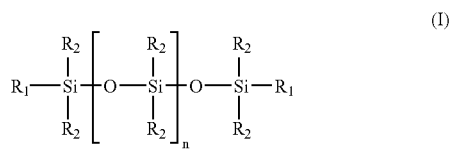

in which:

$R_1$, which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, optionally comprising at least one functional group, n is an integer wherein the polysiloxane of formula (I) has a kinematic viscosity ranging from 1 to $1\times10^6$ mm²/s; and (b) at least one silicone compound comprising at least one and not more than two groups capable of reacting with the groups $R_1$ of the polysiloxane (a), wherein:

at least one of the compounds of type (a) and (b) comprises an aliphatic group comprising an ethylenic unsaturation, and (2) at least one additional silicone, and (3) at least one cationic surfactant, wherein the at least one additional silicone comprises an insoluble silicone.

97. An aqueous or aqueous-alcoholic lotion according to claim 96, said lotion being suitable for skin care or for hair care.

98. A gel, a milk, a cream, an emulsion, a thickened lotion or a mousse according to claim 96, wherein said gel, milk, cream, emulsion, thickened lotion or mousse is suitable to be applied to at least one keratin material chosen from skin, nails, eyelashes, lips and hair.

99. A detergent composition comprising a washing base according to claim 96, wherein said composition is chosen from shampoos, shower gels, bubble baths and make-up-removing products.

100. A detergent composition comprising a washing base according to claim 96, wherein said washing base comprises at least one surfactant chosen from anionic, amphoteric, nonionic and cationic surfactants.

101. A detergent composition according to claim 100, wherein said at least one surfactant is present in an amount effective to provide foaming power and detergent power.

102. A detergent composition comprising a washing base according to claim 100, wherein said washing base is present in an amount ranging from 4% to 50% by weight, relative to the total weight of the final composition.

103. A detergent composition comprising a washing base according to claim 102, wherein said washing base is present in an amount ranging from 6% to 35% by weight, relative to the total weight of the final composition.

104. A detergent composition comprising a washing base according to claim 103, wherein said washing base is present in an amount ranging from 8% to 25% by weight, relative to the total weight of the final composition.

105. A process of washing or caring for a keratin material comprising applying to said keratin material a composition comprising, in a cosmetically acceptable medium, (1) at least one silicone copolymer with a dynamic viscosity ranging from $1\times10^6$ to $100\times10^6$ cP, resulting from the addition reaction, in the presence of a catalyst, of:

(a) at least one polysiloxane of formula (I):

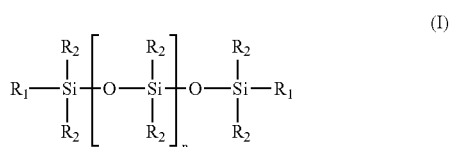

in which:

$R_1$, which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, optionally comprising at least one functional group, n is an integer wherein the polysiloxane of formula (I) has a kinematic viscosity ranging from 1 to $1\times10^6$ mm²/s; and (b) at least one silicone compound comprising at least one and not more than two groups capable of reacting with the groups $R_1$ of the polysiloxane (a), wherein:

at least one of the compounds of type (a) and (b) comprises an aliphatic group comprising an ethylenic unsaturation, and (2) at least one additional silicone, and (3) at least one cationic surfactant, wherein the at least one additional silicone comprises an insoluble silicone.

106. A process for treating a keratin material comprising applying to said keratin material a composition comprising, in a cosmetically acceptable medium, (1) at least one silicone copolymer with a dynamic viscosity ranging from $1\times10^6$ to $100\times10^6$ cP, resulting from the addition reaction, in the presence of a catalyst, of:

(a) at least one polysiloxane of formula (I):

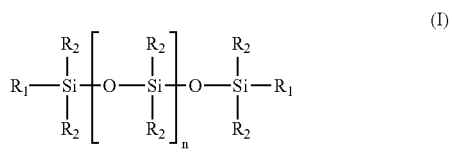

in which:

$R_1$, which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, optionally comprising at least one functional group, n is an integer wherein the polysiloxane of formula (I) has a kinematic viscosity ranging from 1 to $1\times10^6$ mm$^2$/s; and (b) at least one silicone compound comprising at least one and not more than two groups capable of reacting with the groups $R_1$ of the polysiloxane (a), wherein:

at least one of the compounds of type (a) and (b) comprises an aliphatic group comprising an ethylenic unsaturation, and (2) at least one additional silicone, and (3) at least one cationic surfactant, wherein the at least one additional silicone comprises an insoluble silicone, and optionally rinsing said composition out with water.

107. A process for washing or treating a keratin material according to claim 106, wherein said keratin material is chosen from hair, skin, eyelashes, eyebrows, nails, lips and scalp.

108. A process for manufacturing a cosmetic product comprising including in said product (1) at least one silicone copolymer with a dynamic viscosity ranging from $1\times10^6$ to $100\times10^6$ cP, resulting from the addition reaction, in the presence of a catalyst, of:

(a) at least one polysiloxane of formula (I):

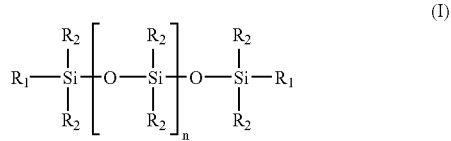

in which:

$R_1$, which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, optionally comprising at least one functional group, n is an integer wherein the polysiloxane of formula (I) has a kinematic viscosity ranging from 1 to $1\times10^6$ mm$^2$/s; and (b) at least one silicone compound comprising at least one and not more than two groups capable of reacting with the groups $R_1$ of the polysiloxane (a), wherein:

at least one of the compounds of type (a) and (b) comprises an aliphatic group comprising an ethylenic unsaturation, and (2) at least one additional silicone and (3) at least one cationic surfactant, wherein the at least one additional silicone comprises an insoluble silicone.

109. A composition according to claim 15, wherein the at least one additional silicone is polydimethylsiloxane.

110. A composition according to claim 109, wherein the at least one silicone copolymer with a dynamic viscosity ranging from $1\times10^6$ to $100\times10^6$ cP, is the copolymer polydimethylsiloxane containing α,ω-vinyl groups/polydimethylsiloxane containing α,ω-hydrogeno groups.

111. A composition according to claim 110, wherein the composition is a rinse-out conditioner for hair.

112. A rinse out conditioner for the hair comprising, in a cosmetically acceptable medium, (1) at least one silicone copolymer with a dynamic viscosity ranging from $1\times10^6$ to $100\times10^6$ cP, resulting from the addition reaction, in the presence of a catalyst, of:

(a) at least one polysiloxane of formula (I):

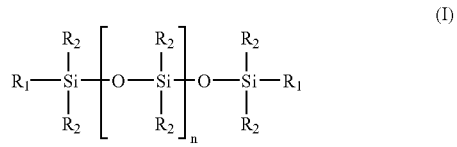

in which:

$R_1$, which may be identical or different, are independently chosen from groups that can react by chain addition reaction, $R_2$ in formula (I), which may be identical or different, are independently chosen from alkyl, alkenyl, cycloalkyl, aryl, hydroxyl, and alkylaryl groups, optionally comprising at least one functional group, n is an integer wherein the polysiloxane of formula (I) has a kinematic viscosity ranging from 1 to $1\times10^6$ mm$^2$/s; and (b) at least one silicone compound comprising at least one and not more than two groups capable of reacting with the groups $R_1$ of the polysiloxane (a), wherein:

at least one of the compounds of type (a) and (b) comprises an aliphatic group comprising an ethylenic unsaturation, wherein said at least one silicone copolymer with a dynamic viscosity ranging from $1\times10^6$ to $100\times10^6$ cP, is a cationic emulsion comprising a copolymer of polydimethylsiloxane containing α,ω-vinyl groups/polydimethylsiloxane containing α,ω-hydrogeno groups;

(2) at least one additional silicone in the form of a polydimethylsiloxane, wherein the at least one additional silicone comprises an insoluble silicone;

(3) at least one cationic surfactant; and (4) at least one alcohol.

* * * * *

UNITED STATES PATENT AND TRADEMARK OFFICE
CERTIFICATE OF CORRECTION

PATENT NO.         : 7,223,384 B1
APPLICATION NO. : 09/692749
DATED              : May 29, 2007
INVENTOR(S)       : Sandrine Decoster et al.

Page 1 of 1

It is certified that error appears in the above-identified patent and that said Letters Patent is hereby corrected as shown below:

On the Title Page, Item (57), in the Abstract, lines 6-7, "regressing" should read --regreasing--.

In claim 60, column 25, line 61, "$R_{15}$, radicals" should read --$R_{15}$ radicals--.

In claim 86, column 28, line 1, "β3-hydroxyethyl" should read --β-hydroxyethyl--.

In claim 86, column 28, line 7, "chosen form" should read --chosen from--.

In claim 108, column 31, line 51, "silicone and" should read --silicone, and--.

Signed and Sealed this

Fourteenth Day of August, 2007

JON W. DUDAS
*Director of the United States Patent and Trademark Office*